(12) United States Patent
Triantafyllou

(10) Patent No.: US 6,190,708 B1
(45) Date of Patent: Feb. 20, 2001

(54) ENZYME PREPARATIONS FOR MODIFYING CEREAL SUSPENSIONS

(75) Inventor: Angelika Oste Triantafyllou, Lund (SE)

(73) Assignee: Cereal Base CEBA AB, Malmo (SE)

( * ) Notice: Under 35 U.S.C. 154(b), the term of this patent shall be extended for 0 days.

(21) Appl. No.: 09/302,127

(22) Filed: Apr. 29, 1999

Related U.S. Application Data

(60) Provisional application No. 60/106,224, filed on Oct. 30, 1998, and provisional application No. 60/104,706, filed on Oct. 19, 1998.

(51) Int. Cl.$^7$ .................................................. A23L 1/105
(52) U.S. Cl. ........................................... 426/28; 426/618
(58) Field of Search .................................. 426/44, 18, 20, 426/21, 28, 52, 618, 629, 456, 459, 460, 462, 463

(56) References Cited

U.S. PATENT DOCUMENTS

| | | | |
|---|---|---|---|
| 4,834,988 | * 5/1989 | Karwowski et al. | 426/20 |
| 4,996,063 | 2/1991 | Inglett | 426/21 |
| 5,686,123 | 11/1997 | Lindahl et al. | 426/28 |

FOREIGN PATENT DOCUMENTS

| | | | |
|---|---|---|---|
| 83106388 | 1/1984 | (EP) | C12P/19/24 |
| 86850418 | 8/1987 | (EP) | C12P/19/14 |
| 93304705 | 1/1994 | (EP) | A23L/1/308 |
| 1495220 | 12/1977 | (GB) | C13K/1/06 |
| 95/27407 | 10/1995 | (WO) | A23L/1/105 |

OTHER PUBLICATIONS

Kessler, H.G., Kessler, Verlay A. Food Engineering and Dairy Technology, 1981, Chapter 6, pp. 139–207.

* cited by examiner

*Primary Examiner*—Keith D. Hendricks
(74) *Attorney, Agent, or Firm*—Simpson, Simpson & Snyder, L.L.P.

(57) ABSTRACT

The present invention provides efficient, selective and economical methods for producing cereal suspensions having the aroma and/or flavor of natural cereals and for modifying the viscosity and/or sugar kind of cereal suspensions. The methods include treating a cereal substrate suspension with an enzyme preparation which comprises at least one hydrolase having the ability to hydrolyze α-glycosidic bonds and having no glucanase and proteinase effect. The hydrolase may be selected from the group consisting of β-amylase, α-amylase, amyloglucosidase and pullulanase, with the proviso that when the enzyme preparation comprises β-amylase or (α-amylase there is always a mixture of at least one other of the α-glycosidic hydrolases. In addition to the above-identified hydrolases, the enzyme preparations of the present invention may further comprise an isomerase, such as glucose isomerase.

21 Claims, No Drawings

ENZYME PREPARATIONS FOR MODIFYING CEREAL SUSPENSIONS

CROSS REFERENCE TO RELATED APPLICATIONS

This application claims the benefit of U.S. Provisional Application Ser. No. 60/106,224 filed Oct. 30, 1998 and U.S Provisional Application Ser. No. 60/104,706 filed Oct. 19, 1998.

FIELD OF THE INVENTION

The present invention relates to enzyme suspensions comprising enzyme preparations for enzymatic hydrolysis of cereal starch. In another aspect it relates to methods of producing homogeneous and stable cereal suspensions prepared by using the enzyme preparations.

BACKGROUND OF THE INVENTION

The beneficial health effects of dietary fibers are well-known. In this context there has been a growing interest in food products made from grains, such as oats and barley.

In many respects, oats are different than other grains. They have higher protein and fat content than comparable cereals as well as a high β-glucan content.

In recent years, there has been a growing interest in food products made from oats. The main reason for this is that oat fibers have been found to have a wholesome effect by lowering the serum cholesterol level of hypercholesteremic individuals. Another reason is that oats contain protein of high food value as well as a considerable proportion of mono and polyunsaturated fats. In addition, oats contain many essential amino acids and minerals.

A great advantage of oats is that the whole grain can be used for making various products once the hull has been removed. In oats, the most nutritious substances are distributed fairly evenly in the whole grain. In other grains, the nutritious substances are frequently concentrated in specific parts of the grain.

The nutritional aspects of oat components have prompted the introduction of oats or parts thereof into several different food products. For instance, U.S. Pat. No. 4,996,063 (G. F. Inglett) discloses the preparation of water-soluble dietary fibre compositions by treating ground oat products with α-amylases. The α-amylase serves to thin the oat starch, and any α-amylase may thus be used. The produced pulverulent dietary fibre compositions are used as additives in food products, such as fat substitutes. However, these products not only lack desirable aromatics of natural oats, but are also deprived of agreeable natural oat flavorings.

U.S. Pat. No. 5,686,123 (to L. Lindahl et al) discloses a homogeneous and stable cereal suspension having the taste and aroma of natural oats. The disclosed cereal suspension is prepared by treating a suspension of oatmeal with β-amylase, which has no glucanase and proteinase activity, in a first enzyme treatment step which specifically generates maltose and maltodextrin units. Then the suspension is treated with α-amylase, which also has no glucanase and proteinase activity, in a second enzyme treatment step which specifically generates maltose units. This oat suspension is a milky product which can be used as an alternative to milk, especially for lactose-intolerant people. It may also be used as the basis of or an additive in the manufacture of ice-cream, gruel, yogurt, milkshakes, health drinks and snacks. However, this process is time consuming because of the sequential treatments with different hydrolases, thereby increasing the cost of production. Moreover, sequential enzyme treatments eliminate any possible positive synergic effects that may occur when combining of enzymes. Furthermore, the overall viscosity and/or sugar content of the cereal suspension cannot be efficiently controlled or manipulated.

In view of these shortcomings, there is a need for enzyme preparations that hydrolyze cereal starch in a more cost-efficient and timely manner while producing a cereal suspension product that retains the flavoring and aromatic qualities of natural cereal and in which the viscosity, sugar content, and overall texture can be regulated or modified for a preferred end product.

SUMMARY OF THE INVENTION

For purposes of this invention, the terms and expressions below appearing in the specification and claims are intended to have the following meanings:

"Preprocessed cereal suspension" as used herein means a product that has been previously processed by the method disclosed in U.S. Pat. No. 5,686,123.

"Cereal substrate" as used herein means a suspension selected from the group consisting of cereal meal suspension, preprocessed cereal suspension and mixtures thereof "Oatmeal suspension" as used herein means a suspension comprising oat flour and/or rolled oats.

Accordingly, it is a principal object of the present invention to provide an enzyme modified suspension comprising a cereal substrate suspension and an enzyme preparation for enzymatic hydrolysis of constituents in the cereal substrate suspension whereby the specific properties of the cereal substrate suspension, such as viscosity and/or sugar ratio content modified and/or manipulated by combinations of various hydrolases and isomerases.

It is another object of the present invention to provide an efficient, selective and economical method for producing a cereal suspension having the aroma and/or flavor of natural cereals and having the unexpected improvement of regulating the viscosity and/or sugar content of the cereal suspension through treatment with a spectrum of new enzyme preparations.

It is an additional object of the present invention to provide a homogeneous and stable cereal suspension having the aroma and/or flavor of natural cereals and containing intact β-glucans that are components of a cereal substrate suspension.

A still further object of the present invention is to provide a method for preparing the homogeneous and stable cereal suspension having the aroma and taste of natural cereals and containing intact β-glucans.

All of the above objects may be accomplished by an enzyme modified suspension comprising a cereal substrate suspension and an enzyme preparation for enzymatic hydrolysis of constituents in the cereal substrate suspension. The enzyme preparation comprises at least one hydrolase with the ability to hydrolyze α-glycosidic bonds of the constituents of a cereal substrate suspension, and optionally, combining the at least one hydrolase with an isomerase. The constituents may include, but are not limited to, amylose, amylopectin, maltodextrins, maltose, maltotriose and a mixture thereof. More specifically, the above objects may be accomplished by an enzyme modified suspension comprising a cereal substrate suspension and an enzyme preparation wherein the enzyme preparation comprises at least one hydrolase having the ability to hydrolyze α-glycosidic bonds of constituents of a cereal substrate suspension. It is preferred that the enzyme preparation has no glucanase and/or proteinase activity. The preferred hydrolase may be selected from the group consisting of β-amylase, α-amylase, amyloglucosidase and pullulanase, with the proviso that when the enzyme preparation comprises β-amylase or α-amylase there is a mixture of at least one other of the named α-glycosidic hydrolases. It is further preferred that when the enzyme preparation comprises both β-amylase and α-amylase they are combined simultaneously in the cereal substrate suspension. In addition to the above-identified hydrolases, the enzyme preparations of the present invention may further comprise an isomerase, such as glucose isomerase.

The previously discussed enzyme preparations may be utilized to produce a homogeneous and stable improved cereal suspension having the aroma and taste of natural cereals and containing intact β-glucans, the improved cereal suspension prepared by the method comprising the steps:

a) providing a cereal substrate suspension;
b) treating the cereal substrate suspension of step (a) with an enzyme preparation as previously discussed, namely an enzyme preparation for enzymatic hydrolysis of a cereal starch in the suspension comprising at least one hydrolase enzyme having the ability to hydrolyze α-glycosidic bonds. Preferably, a α-glycosidic hydrolase is selected from the group consisting of β-amylase, α-amylase, amyloglucosidase, pullulanase and mixtures thereof, with the proviso that when the enzyme preparation comprises β-amylase or α-amylase there is a mixture of at least one other of the named α-glycosidic hydrolases.

It is preferred that when the enzyme preparation comprises both β-amylase and α-amylase, the enzymes are introduced simultaneously to the cereal substrate suspension.

The method of making the homogeneous and stable improved cereal suspension may also include performing at least one finishing process step on the enzyme treated suspension of step (b) for making the cereal suspension.

The finishing process step which may improve the shelf-life of the cereal suspension or end product can include: removing coarse particles by centrifuging or decanting; homogenizing the enzyme treated suspension; and/or subjecting the product to Ultra High Temperature (UHT) treatments disclosed in *Food Engineering and Dairy Technology*, H. G. Kessler, Verlay A. Kessler, 1981, Chapter 6, pp. 139–207, the contents of which are incorporated by reference herein. After UHT the product may be aseptically packed. Additional processes for improved shelf life may include pasteurizing and refrigeration until used; or the end product may be evaporated and subsequently spray dried to yield a stable powder. Preferably, the enzyme treated suspension is homogenized and subjected to UHT and aseptically packed.

Enzyme activity may be terminated or removed from the enzyme treated suspension before processing for improved shelf life. As an alternative, the enzyme activity may be terminated during some of the processes that improve the self-life of the product, such as the UHT process.

Optionally, the enzyme treated suspension of step (b) may be treated sequentially with a second enzyme preparation comprising at least one hydrolase enzyme having the ability to hydrolyze α-glycosidic bonds selected from the group consisting of β-amylase, α-amylase, amyloglucosidase, pullulanase and a mixture thereof. Further in this respect, the above improved cereal substrate suspensions may be treated by combining an isomerase, such as glucose isomerase with the hydrolases of the enzyme preparations.

The homogeneous and stable improved cereal suspension having the aroma and taste of natural cereals and containing intact β-glucans may also be prepared by the method comprising the steps:

a) preparing a cereal meal suspension,
b) treating the cereal meal suspension of step (a) with β-amylase and followed sequentially with the introduction of α-amylase;
c) treating the enzyme treated suspension of step (b) with an enzyme preparation as discussed previously herein above comprising at least one hydrolase enzyme having the ability to hydrolyze α-glycosidic bonds. Preferably, an α-glycosidic hydrolase is selected from the group consisting of β-amylase, α-amylase, amyloglucosidase, pullulanase and a mixture thereof with the proviso that when the enzyme preparation comprises β-amylase or α-amylase there is a mixture of at least one other of the named α-glycosidic hydrolases.

It is preferred that when the enzyme preparation comprises both β-amylase and α-amylase, the enzymes are introduced simultaneously to the cereal substrate suspension.

The enzyme treated suspension of step (b) and (c) may be further treated by discontinuing enzymatic activity and/or further performing a finishing process step.

DETAILED DESCRIPTION OF THE PREFERRED EMBODIMENTS

According to the invention, there is provided an enzyme preparation for enzymatic hydrolysis of constituents in a cereal substrate suspension, comprising at least one hydrolase enzyme having the ability to hydrolyze α-glycosidic bonds. The hydrolases may be selected from the group consisting of β-amylase, α-amylase, amyloglucosidase pullulanase and mixtures thereof Preferably, when the enzyme preparation comprises β-amylase or amylase there is a mixture of at least one other of the named α-glycosidic hydrolases, and more preferably, when there are two or more enzymes combined in the enzyme preparation, the enzymes are introduced simultaneously to the cereal substrate suspension. In addition to the above-identified hydrolases, the enzyme preparation may further comprise an isomerase, such as glucose isomerase.

In preferred embodiments of the invention, the enzyme preparations may comprise pullulanase solely; amyloglucosidase solely; or several different combinations of hydrolases including: a mixture combining β-amylase with pullulanase; a mixture combining β-amylase, pullulanase and amyloglucosidase; a mixture combining β-amylase and α-amylase; and a mixture combining α-amylase, β-amylase and amyloglucosidase. Any of the above enzyme preparations comprising a hydrolase alone or in combination with another may further comprise an isomerase, such as glucose isomerase.

The enzyme preparations of the present invention convert cereal starch, which comprises both amylose and amylopectin, to large molecular weight maltodextrins and lowmolecular-weight compounds of various degrees of modification, such as maltotriose, maltose and glucose. For instance, β-amylase hydrolyzes α-1–4 glycosidic bonds sequentially from the non-reducing terminal end of amylose and amylopectin with a cleaved product of maltose; α-amylase hydrolyzes internal α-1–4 glycosidic bonds on both amylose and amylopectin with a cleaved maltodextrin; and amyloglucosidase hydrolyzes α-1–4 and 1–6 glycosidic bonds on the non-reducing end of the starch releasing glucose molecules. Therefore, a combination of hydrolases having the ability to hydrolyze α-glycosidic bonds will provide various ratios of maltodextrin/sugar in an enzyme treated cereal suspension.

The choice of enzymes and the reaction time determine the degree of degradation and product spectra. Different species of di-and mono-saccharides are produced by using different enzyme preparations which include the combination of at least one α-glycosidic hydrolase and/or an isomerase. The end products could include the di-saccharide, maltose, and the mono-saccharides, fructose and glucose. For example, the debranching enzyme pullulanase together with β-amylase will accumulate large amounts of maltose. Amyloglucosidase and glucose isomerase may result in the production of fructose and glucose. When combining β-amylase and α-amylase, the α-amylase promotes the action of the β-amylase thereby obtaining maltose and maltodextrin units while using a smaller amount of enzymes then if enzymes are used separately. A cereal starch may be converted entirely to low-molecular-weight compounds, such as glucose by combining, for example, β-amylase, α-amylase and amyloglucosidase. Glucose isomerase, solely, will result in the production of fructose when added to a cereal substrate that already contains glucose. In the alternative, the enzyme preparation wherein β-amylase, α-amylase and amyloglucosidase are combined with glucose isomerase may also produce a product with high levels of fructose.

The enzyme preparations, that being a single enzyme or a mixture of enzymes may treat a cereal substrate suspension of the present invention by introducing free enzymes directly into a cereal substrate suspension, or in the alternative introducing the cereal substrate suspension to a vessel containing immobilized enzymes.

Free enzymes as used herein means enzymes which are free to move in the suspension and are not restricted by containment or affixed to a substrate. Usually, free enzymes or cells are not re-used because they are too small to filter and recovery may become cost prohibitive. Hence, elimination of the biocatalytic activity of free enzymes in the present invention is usually accomplished by denaturing of the enzyme.

Immobilized enzymes as used herein means free enzymes that are physically confined by different methods including, but not limited to, semi-permeable membranes, hollow bore fibers, or ultrafiltration membranes. Immobilized enzymes, whether soluble or insoluble, allow for the simultaneous immobilization of many enzymes, selectively controlling substrates and products through membrane selectivity. As used in the present invention immobilized enzymes provide for ease of loading and treating the cereal meal suspension in a continuous mode reactor.

The benefits of immobilized enzymes include complete recovery of the enzymes from the reaction mixture whether used in a batch or continuous mode operation. Thus, the enzymes can be used repeatedly without any contamination of the final product and without the need to heat the product so as to denature the enzyme. Also, larger concentrations of immobilized enzyme can be utilized because the immobilized enzymes can be recovered and re-used, resulting in a shortening of reaction time and/or the size of the vessel needed to carry out the reaction. Another advantage is the virtual absence of enzyme in the final product so that the enzyme only has to be approved as a food processing aid and not as a food additive even when heating and subsequent enzyme inactivation is not included in the process.

It is further contemplated by the inventors that the enzymes used to prepare the enzyme modified suspensions and/or the homogeneous and stable improved cereal suspension may include enzymes derived from whole cells, organelles, or even microorganisms used as biological catalysts in a fermentation process.

In the present invention the overall conditions including temperature, pH and the addition of other substrates, such as enzyme cofactors or buffering agents will determine the enzyme activity, and therefore, the yield and quality of the end product. It is known that enzymes may be extracted from different sources but can catalyze the same reaction. For instance, α-amylase from the fungal organism *Aspergillus oryzae* has a optimum pH of 4.7 and an optimum temperature of 50° C., while α-amylase from the bacterium *Bacillus lichenformis* has a pH optimum of 7.5 and an optimum temperature of 90° C. Thus understood, the optimum conditions, including the amount of enzyme, the temperature of the slurry, the agitation time and the pH value are optimized to obtain a final product of suitable viscosity. Techniques used for determining optimal parameters are well known and widely used in the art.

The enzyme preparations of the present invention may be used to provide a homogeneous and stable improved cereal suspension having the aroma and taste of natural cereals and containing intact β-glucans. The enzyme preparations are used to treat a cereal substrate which may include a cereal meal suspension, a preprocessed cereal suspension or a mixture thereof.

In one embodiment, the cereal substrate suspension is a cereal meal suspension. The cereal meal suspension is prepared by dry- or wet-grinding rolled cereals, or otherwise, heat- and water-treated cereals to.meal and suspending the cereal meal in water to form a cereal meal suspension. Optionally, the suspension may be centrifuged or decanted in order to remove coarse fibre particles before being treated with the enzyme preparation.

Conveniently, the cereal meal suspension is prepared on the basis of commercially produced, pregelatinized rolled oats retaining the original taste and aroma of the oats. The rolled oats are ground to oatmeal by total, dry or wet grinding. In dry grinding, the oatmeal is suspended in water, preferably at a temperature of 50°–65° C. Also in wet grinding, water is used preferably at a temperature of 50°–65° C. Especially good results are obtained if the water has been deionized.

For a majority of starch contained within the cereal meal the heating of the suspension to a temperature between 50° to 65° C. gelatinizes the cereal starch for easier hydrolyzation. However, some oats contain resistant starches that are not gelatinized at these temperatures, and therefore, are not easily hydrolyzed by the enzyme preparations of the present invention. In this instance, it has been found to be beneficial to initially hydrolyze the non-resistant starch in a first enzyme treating step with the enzyme preparations of the present invention and then subjecting the suspension to higher temperatures, preferably above 100° C. to gelatinize the resistant starch. The suspension is subsequently cooled to a workable temperature and standard conditions. The suspension is the retreated with the enzyme preparations of the present invention. Accordingly, the non-resistant starch in the cereal meal suspension may be hydrolyzed with the enzyme preparations of the present invention and then the suspension is heat treated to a higher temperature to solubilize the resistant starch. The suspension is cooled to a temperature that is suitable for enzymatic activity and then retreated with an enzyme preparation of the present invention. This method will allowed for more complete hydrolyzation of substantially all the cereal starch including the resistant starch in the cereal meal suspension.

Suitably, the slurry or suspension has a weight ratio of meal to water in the range of about 1:6 to about 1:9, which corresponds to a dry solids content of about 10 to about 15% w/v. The suspension is agitated until the meal has been dispersed. The slurry should have a pH of at least 5 to about 8. This pH range has been found to be effective when adding the enzyme preparations of the present invention. Within this pH range the enzyme preparations have acceptable catalytic activity and can avoid the use of additives to alter the pH.

In order to remove the coarse particles, the suspension can then be centrifuged or decanted at 350–450 G for about 10–15 minutes.

In a further embodiment of the present invention, a preprocessed cereal suspension may be used. The preprocessed cereal suspension is defined as that which is first prepared according to the methods disclosed in U.S. Pat. No. 5,686,123. The cereal meal suspension is treated with β-amylase in a first enzyme treatment step which specifically generates maltose units and has no glucanase and proteinase activity, to a viscosity of 3–0.1 Pas at the shear rate of 10–100 s$^{-1}$. Then the suspension is treated with (α-amylase in a second enzyme treatment step which specifically generates maltose units and has no glucanase and proteinase activity, to a viscosity of <0.5 Pas at the shear rate of 10–100 s$^{-1}$. This preprocessed cereal suspension may then be further treated by the enzyme preparations of the present invention. Optionally, the preprocessed cereal suspension may be homogenized and/or subjected to UHT treatment.

The cereal substrate suspension is treated with the enzyme preparations under carefully regulated operating temperatures. The temperature is chosen to favor the enzymatic performance allowing both fast hydrolytic rates and good enzyme stability. A temperature from about 40° C. to a temperature below that which would denature the enzyme or combination of enzymes is generally employed, preferably from about 50° to about 90° C. depending on the enzyme. At lower temperatures the enzyme activity may be low and at higher temperatures the enzyme stability may be low. Accordingly, the temperature of the catalytic reaction is chosen to optimize production of the end products while maintaining the stability of the enzyme preparation. The present invention is also applicable to thermostable starch degrading enzymes, in which case the operation conditions can be adapted to the characteristics of such enzymes.

A hydrolase and/or combination of several hydrolases are introduced to a cereal substrate suspension in a sufficient amount to hydrolyze α-glycosidic bonds of constituents in the cereal substrate suspension to provide an end product with the desired viscosity. The combination of enzymes and amount of each specific enzyme results in suspensions that contain different sugars, but also in different amounts. High content of low molecular sugars, such as maltose and glucose will yield an end product suspension with less viscosity. In contrast, a higher content of maltodextrin, which is considered a higher molecular weight molecule yields a product with greater viscosity that may be used in soups or yogurts because of thicker consistency.

Accordingly, varying the kind and/or the amount of enzymes in the mixture will yield specially designed products. Using a specific combination of enzymes helps to standardize the process so that the end product is related to the enzyme combination whereby reaction time and other process parameters do not greatly affect the end product. In carrying out the present invention, it is generally advantageous to employ between about 1 to about 100 ml of enzyme preparation per kilogram of oats or other grain material which make up the cereal substrate suspension. The suspension may be treated with the enzyme preparation to produce a final product which has the viscosity of about water or about 10 mPas to about several hundreds of mPas at a sheer rate of about 500 to about 1000s$^{-1}$.

Generally, the grain that is incorporated into the cereal meal suspension may be any starting grain material including but not limited to oats, barley, rice, wheat, maize, rye, sorghum, triticale and pearl millet. Preferably, the grain is oats. As stated above, oats have properties that make them especially desirable from a consumer point of view because of the large amounts of high molecular weight β-glucans which are natural hydrocolloids. In suspensions produced by enzymatic hydrolysis with the enzyme preparations of the present invention, the β-glucans found in oats function as indigenous stabilizers. Therefore, the cereal suspensions of the present invention may be used in food for thickening, gelling or emulsion stabilizing effects.

The sweetness of an enzyme modified suspension or a homogeneous and stable improved cereal suspension can be regulated and/or manipulated using appropriate enzyme preparations. In fact, the enzyme preparations of the present invention may be introduced in several steps to tailor-make the end product. For instance, an enzyme preparation comprising α- and β-amylase may produce a high level of maltose. With a second treatment of an enzyme preparation comprising amyloglucosidase and/or glucose isomerase the maltose can be converted to glucose and fructose. The production of glucose, and, particularly, of fructose will result in a sweeter suspension than one containing mainly maltose. A suspension comprising fructose has the significant advantage that it can be consumed by diabetics without adverse affects.

The specific type of sugar affects not only the properties of the suspension but also the organoleptic properties of products produced by using the suspensions. By altering the sugar profile, it is possible to tailor-make suspensions that yield end products having functional properties, such as viscosity; nutritional properties and sugar ratio content to meet the needs of the final user.

Enzymatic activity may be discontinued or terminated in the enzyme modified cereal suspension or the enzyme treated cereal suspension by any method well known in the art, including denaturation, centrifuge, chromatography for free enzymes and/or removal of the suspension from contact with immobilized enzymes. Preferably, The enzyme reaction is terminated by heating the cereal suspension to at least 80° C., and preferably, between about 80° to 90° C.

As an alternative the enzyme activity may be discontinued terminated during the final process steps that improve the shelf-life of the product. Representative final process steps may include: removing coarse particles by centrifuging or decanting; homogenizing the enzyme treated suspension at a temperature of about 42 to about 45° C., at a pressure of about 200 to about 250 bar; or subjecting the product to Ultra High Temperature (UHT) treatments disclosed in Food Engineering and Dairy Technology, H. G. Kessler, Verlay A.

Kessler, 1981, Chapter 6, pp. 139–207, the contents of which are incorporated by reference herein. After UHT the product may be aseptically packaged. Additional processes for improved shelf life may include pasteurizing and refrigeration until used; or the end product may be evaporated and subsequently spray dried to yield a stable powder.

Cereal suspensions according to the invention can be used in the same fields as the products disclosed in U.S. Pat. No. 5,686,123, that is as a milk substitute, as the basis of or an additive in the manufacture of ice-cream, gruel, yogurt, milkshakes, and snacks.

The invention will now be described in more detail by the following non-limiting examples.

EXAMPLE 1

Pregelatinized rolled oats were wet-milled at a temperature of about 52° to about 63° C. The concentration of the suspension was about 10 to about 15% w/v. An enzyme preparation according to the invention which comprised barley □-amylase (Genencor Intl., Rochester, N.Y., USA; or Rhodia Ltd, Cheshire, UK) and pullulanase, a debranching enzyme, e.g. Promozyme (Novo Nordisk, Bagsvaerd, Denmark), was added to the cereal meal suspension at a concentration of approximately 2 ml per kg of oats and at a temperature of about 58° to about 61° C. The concentration of the enzymes in the enzyme preparation was about 500 to about 1000 DP° and about 150 to about 300 PU (pullulanase units) per ml, respectively. The enzyme preparation was allowed to act for 1–2 hours, or until the viscosity of the suspension dropped to about 20 to about 40 mPas at a shear rate of around $700\ s^{-1}$. The product contained large amounts of maltose. The majority of starch (approximately 60% of the oats) was converted to maltose.

The suspension was then heated to about 85° to about 90° C. to inactivate the enzymes. The product was decanted to remove the excess of non-soluble fibre, and homogenized. Optionally the product could be UHT treated and aseptically packed, pasteurized and kept refrigerated until used, or it is evaporated and subsequently spray dried to yield a stable powder.

EXAMPLE 2

Pregelatinized rolled oats were milled as in Example 1. An enzyme preparation according to the invention which comprised barley β-amylase (Genencor Intl., Rochester, N.Y., USA; or Rhodia Ltd, Cheshire, UK), pullulanase, a debranching enzyme, e.g. Promozyme (Novo Nordisk, Bagsvaerd, Denmark) and amyloglucosidase, e.g., AMG (Novo Nordisk, Bagsvaerd, Denmark) or Optidex (Genencor Intl., Rochester, N.Y., USA) was added to the oat meal suspension at a concentration of about 3 to about 4 ml per kg oats and at a temperature of about 58° to about 61° C. The concentration of these enzymes in the enzyme preparation was about 400 to about 700 DP°, about 100 to about 200 PU (pullulanase units) and about 90 to about 110 AGU per ml, respectively. The enzyme preparation was allowed to act for about 1 to about 2 hours, or until the viscosity of the suspension dropped to about 20 to about 40 mPas at a shear rate of $700\ s^{-1}$. The product contained large amounts of glucose. Finally, the suspension was heated and treated as in Example 1.

EXAMPLE 3

Pregelatinized rolled oats were milled as in Example 1. An enzyme preparation according to the invention which comprised a mixture of β-amylase (Genencor Intl., Rochester, N.Y., USA; or Rhodia Ltd, Cheshire, UK) and endo-acting α-amylase, e.g. Fungamyl (Novo Nordisk, Bagsvaerd, Denmark) or Mycolase (Genencor Intl., Rochester, N.Y., USA), was added to the cereal meal suspension at a concentration of approximately 2 ml per kg of oats and at a temperature of about 54° to about 57° C. The concentration of these enzymes in the enzyme preparation was about 1400 to about 1600 DP° and about 30 to about 70 AU (amylase units) per ml, respectively. The enzyme preparation was allowed to act for about 1 hour, or until the viscosity of the suspension dropped to about 20 to about 40 mPas at a shear rate of about $700\ s^{-1}$. Most of the oat starch (60–70%) was converted to maltose and the rest was present as maltodextrins (step 1) Then (in step 2), another exo-acting enzyme was added, e.g. amyloglucosidase AMG (Novo Nordisk, Bagsvaerd, Denmark) or Optidex (Genencor Intl., Rochester, N.Y., USA), at a dosage of approximately 600 AGU (amyloglucosidase units) per kg of oats. The reaction was terminated when the desired amount of glucose had been produced. For example, 30 minutes after the addition of amyloglucosidase (glucoamylase), the suspension contained equal amounts of maltose and glucose while the maltose content was 50% of the suspension in step 1. The maltose content was high in step 1, and amyloglucosidase rapidly hydrolyzed this substrate. As the maltose content decreased, maltodextrin became the preferred substrate and also became increasingly hydrolyzed. At full conversion all the starch was converted to glucose. Finally, the suspension was heated and treated as in Example 1.

EXAMPLE 4

Pregelatinized rolled oats were milled as in Example 1. An enzyme preparation according to the invention which comprised a mixture of barley β-amylase (Genencor Intl., Rochester, N.Y., USA; or Rhodia Ltd, Cheshire, UK), α-amylase, e.g. Fungamyl (Novo Nordisk, Bagsvaerd, Denmark) or Mycolase (Genencor Intl., Rochester, N.Y., USA) and amyloglucosidase, e.g., AMG (Novo Nordisk, Bagsvaerd, Denmark) or Optidex (Genencor Intl., Rochester, N.Y., USA) was added to the suspension at a dosage of about 3 to about 4 ml per kg oats and at a temperature of about 54° to about 57° C. The concentration of these enzymes in the enzyme preparation was about 700 to about 900 DP°, about 1 to about 35 AU (α-amylase units) and about 200 to about 350 AGU per ml, respectively. The enzyme preparation was allowed to act for about 1–2 hours, or until the viscosity of the suspension dropped to about 20 to about 40 mPas at a shear rate of about $700\ s^{-1}$. Finally, the suspension was heated and treated as in Example 1.

EXAMPLE 5

A suspension of oats was prepared as in U.S. Pat. No. 5,686,123 is treated with an enzyme preparation according to the invention and which comprised barley β-amylase (Genencor Intl., Rochester, N.Y., USA; or Rhodia Ltd, Cheshire, UK) and pullulanase, a debranching enzyme, e.g. Promozyme (Novo Nordisk, Bagsvaerd, Denmark), at a concentration of approximately 2 ml per kg of oats. Alternatively, the suspension was treated with a debranching enzyme, such as pullulanase, e.g. Promozyme (Novo Nordisk, Bagsvaerd, Denmark), at a concentration of approximately 800 PU per kg of oats. Otherwise the conditions were the same as in Example 1. The product was high in maltose and contained essentially no maltodextrins.

EXAMPLE 6

A suspension of oats was prepared as in U.S. Pat. No. 5,686,123 and was treated with the same enzyme preparation as in Example 2, or with amyloglucosidase as in Example 3 (as in step 2). The product contained a decreasing amount of maltodextrins and an increasing amount of glucose as the hydrolytic reaction proceeded.

EXAMPLE 7

To any of the products of Examples 2, 3, 4 and 6, i.e., which contained glucose, there was added an enzyme preparation according to the invention which comprised amyloglucosidase of about 50 to about 60 AGU per ml, e.g., AMG (Novo Nordisk, Bagsvaerd, Denmark) or Optidex (Genencor Intl., Rochester, N.Y., USA) and glucose isomerase (about 3000 GIU per ml), at a concentration of about 18 to about 70 ml per kg of oats, or only glucose isomerase, e.g. Spezyme GI (Genencor Intl., Rochester, N.Y., USA) or Sweetzyme (Novo Nordisk, Bagsvaerd, Denmark), at a concentration of about 50,000-to about 200,000 GIU (glucose isomerase units). Within two (2) hours, 25% of the glucose was converted to fructose.

EXAMPLE 8

Pregelatinized rolled oats were milled as in Example 1. An enzyme preparation according to the invention which comprised a mixture of β-amylase (Genencor Intl., Rochester, N.Y., USA; or Rhodia Ltd, Cheshire, UK), and endo-acting α-amylase, e.g. Fungamyl (Novo Nordisk, Bagsvaerd, Denmark) or Mycolase (Genencor Intl., Rochester, N.Y., USA) was added to the cereal meal suspension at a concentration of approximately 2 ml per kg oats and at a temperature of about 540 to about 57° C. The concentration of these enzymes in the enzyme preparation was about 1400 to about 1600 DP° and about 1 to about 8 AU (α-amylase units) per ml, respectively. The enzyme preparation was allowed to act for approximately 2 hours, or until the viscosity of the suspension dropped to about 45 to about 65 mPas at a shear rate of about 700 s$^{-1}$. One third of the starch was converted to maltose while the rest was present as maltodextrin. The product was quite thick because of the high content of maltodextrin. Finally the suspension was treated as in Example 1.

That which is claimed is:

1. A method of making a modified oat cereal suspension comprising maltose and maltodextrin units, intact β-glucans and proteins by the steps, which comprise:
   (i) providing an oat cereal substrate suspension;
   (ii) providing an enzyme composition comprising β-amylase and α-amylase, and
   (iii) treating said oat cereal substrate suspension (i) with said enzyme composition (ii), wherein said β-amylase and α-amylase enzymes are introduced simultaneously for accelerated enzymatic hydrolysis, reduction of viscosity and regulating sugar content formation of said modified oat cereal suspension, said method allowing use of lesser amounts of said enzymes than otherwise needed when said enzymes are used separately, and
   (iv) performing at least one finishing step on the enzyme modified oat cereal suspension of step (iii).

2. The method according to claim 1 wherein the viscosity ranges from about 20 mPas to about 40 mPas at a sheer rate of about 700 s$^{-1}$.

3. The method according to claim 1 wherein the enzyme composition further comprises an isomerase.

4. The method according to claim 1 wherein the enzymatic activity of the enzyme treated oat cereal suspension of step (iii) is terminated before performing the finishing step (iv).

5. The method according to claim 1 wherein step (iv) comprises at least one finishing step selected from the group consisting of homogenizing, ultra high temperature treatment, pasteurizing, refrigeration, evaporation and spray drying.

6. The method according to claim 1 wherein the oat cereal substrate suspension of step (i) is further treated by removing coarse fibre particles.

7. The method according to claim 1 wherein the oat cereal substrate suspension of step (i) is prepared by grinding rolled oats, heat-treated or water-treated oats to meal and suspending the oat meal in water to form a suspension.

8. The method according to claim 1 wherein the oat cereal substrate suspension of step (i) is treated with β-amylase and subsequently treated with α-amylase prior to the introduction of β-amylase and α-amylase enzymes simultaneously according to step (iii).

9. The method according to claim 8 wherein the enzyme composition further comprises the addition of glucose isomerase.

10. The method according to claim 1 wherein the enzymatic activity of the enzyme treated suspension of step (iii) is terminated before performing step (iv).

11. The method according to claim 1 wherein the enzyme treated suspension of step (iii) is further treated with a second enzyme composition comprising at least one hydrolase enzyme having the ability to hydrolyze α-glycosidic bonds selected from the group consisting of βamylase, α-amylase, amyloglucosidase and pullulanase.

12. The method according to claim 11 wherein the second enzyme composition further comprises glucose isomerase.

13. A product prepared by the method according to claim 1.

14. A product prepared by the method according to claim 2.

15. A product prepared by the method according to claim 3.

16. A product prepared by the method according to claim 8.

17. A product prepared by the method according to claim 9.

18. An enzyme modified oat cereal suspension comprising maltose and maltodextrin units, intact β-glucans and proteins, said enzyme modified oat cereal suspension prepared by the method which comprises the steps of:
   (i) providing an oat cereal substrate suspension;
   (ii) providing an enzyme composition comprising β-amylase and α-amylase, and
   (iii) treating said oat cereal substrate suspension (i) with said enzyme composition (ii), wherein said β-amylase and α-amylase enzymes are introduced simultaneously for accelerated enzymatic hydrolysis, reduction of viscosity and regulating sugar content formation of said modified oat cereal suspension, said method allowing use of lesser amounts of said enzymes than otherwise needed when said enzymes are used separately.

19. The enzyme modified oat cereal suspension according to claim 18, including the performance of at least one finishing step on the enzyme treated oat cereal suspension of step (iii).

20. The enzyme modified cereal suspension according to claim 18, wherein the enzyme modified oat cereal suspension has a viscosity from about 20 mPas to about 40 mPas at a sheer rate of about 700 s$^{-1}$.

21. The enzyme modified cereal suspension according to claim 18 wherein the enzyme composition further comprises an isomerase.

* * * * *